United States Patent
Cooper et al.

(10) Patent No.: US 6,212,950 B1
(45) Date of Patent: Apr. 10, 2001

(54) GLASS INTERLACED FUEL SYSTEM LOW CURRENT RHEOSTAT

(75) Inventors: Richard O. Cooper; Deborah K. Cooper, both of Bluffton, IN (US)

(73) Assignee: CTS Corporation, Elkhart, IN (US)

( * ) Notice: Subject to any disclaimer, the term of this patent is extended or adjusted under 35 U.S.C. 154(b) by 0 days.

(21) Appl. No.: 08/864,711

(22) Filed: May 28, 1997

Related U.S. Application Data

(60) Provisional application No. 60/017,112, filed on May 9, 1996.

(51) Int. Cl.$^7$ ............... G01F 23/36; G01F 23/30; G01F 23/52; G01F 23/60
(52) U.S. Cl. ............... 73/313; 73/305; 73/308; 73/317
(58) Field of Search ............... 73/313, 317, 314, 73/305, 309, 308

(56) References Cited

U.S. PATENT DOCUMENTS

| | | |
|---|---|---|
| 3,613,042 | 10/1971 | Leerkamp et al. . |
| 4,032,881 | 6/1977 | Singleton . |
| 4,318,075 | 3/1982 | Pudelko et al. . |
| 4,500,866 | 2/1985 | Romann et al. . |
| 4,931,764 | 6/1990 | Gaston . |
| 5,051,719 | 9/1991 | Gaston et al. . |
| 5,169,465 | 12/1992 | Riley . |
| 5,746,088 | 5/1998 | Sawert . |

*Primary Examiner*—Hezron Williams
*Assistant Examiner*—Dennis Loo
(74) *Attorney, Agent, or Firm*—Mark P. Bourgeois; Mark W. Borgman

(57) ABSTRACT

A fuel level indicator system that utilizes a resistor card having an arc-shaped resistive path with a first set of spaced apart conductor lines and an arc-shaped resistive ink material overlying the first set of conductor lines. There is provided a first and second set of insulative bars that are screened between and parallel to the first and second sets of spaced apart conductor lines respectively. The bars provide for decreased wear of the fuel level indicator system. The first conductor lines are formed at an angle with respect to a radial line drawn from the center of the resistive path arc. The resistor card also has an arc-shaped continuously solid conductor base and a second set of spaced apart conductor lines extending from the base at an angle with respect to a radial line drawn from the center of the arc-shaped conductor base. The system includes a wiper assembly having a pair of spaced apart arms. Each arm has a plurality of parallel fingers extending from one end. One of the fingers on a first arm engages a conductor line on the resistive path and a second finger on the first arm engages an adjacent conductor line along the resistive path. A first finger on the second arm engages a conductive line on the conductive path; and a second finger engages an adjacent conductor line on the conductive path. The wiper assembly is constructed and arranged to provide rotational movement along the arc-shaped conductive path and arc-shaped resistive path. The system also has a float with an extending lever that is connected to the wiper assembly to produce rotational movement of the wiper assembly as the float moves.

3 Claims, 2 Drawing Sheets

GLASS INTERLACED FUEL SYSTEM LOW CURRENT RHEOSTAT

This application is related to both copending U.S. application Ser. No. 60/017,112 entitled FUEL SYSTEM LOW CURRENT RHEOSTAT, filed May, 9 1996.

BACKGROUND OF THE INVENTION

1. Field of the Invention

The present invention relates to variable resistors and in particular to a ceramic resistor card for use in a transducer for converting a physical position into an electrical signal with interlaced glass fingers for longer wear from wiper contacts.

2. Description of the Related Art

Variable resistors are known for sensing parameters in a variety of applications. For example, the fuel level in an automobile tank is typically measured using a variable resistor having a sweep arm mechanically or electrically coupled to a float located in a fuel tank. The sweep arm position is determined by the level of fuel in the tank and the voltage value sensed across the variable resistor depends on the position of the sweep arm.

The variable resistor typically comprises a resistor card with metalized areas and thick film resistive ink. The thick film ink is deposited in precise areas to interconnect respective metalized areas. There is a wiper blade assembly having contact fingers thereon connected to the sweep arm. As the float raises and lowers according to the fluid level, the wiper contact fingers move along the resistor card in an arcuate path and make corresponding contact with the metalized areas. This results in a voltage change that generates a signal representative of the amount of fuel contained in the tank.

One problem with this type of system is that over the life of a vehicle it must go through thousands of cycles in a harsh environment. The card is often exposed to both fuel and dry conditions as the fluid level is decreased. In addition, the assembly is exposed to severe vibration resulting from the vehicle movement. The result is that wear occurs as the wiper contact fingers go back and forth over the metalizations and the electrical resistance of the metalization portions may increase and cause accuracy problems with the fuel reading. Additionally, the metalized portions may wear to the point that an open circuit results along some given or several metalization locations.

Specifically, there are problems when conductors lines are broken up into finger-like projections or short conductor lines with spaces therebetween. When a wiper blade assembly is rubbed over the spaced apart conductor lines, the edge of each conductor line begins to be worn down from repetitive impact. Additionally, the wiper blade assembly contact fingers are equally worn down faster because of the repetitive impact with the edges of the conductor lines. Further wear is encouraged by the contact fingers bouncing up and down as they travel approximately perpendicular across the orientation of the conductor line sets.

3. Related Art

Examples of patents related to the present invention are as follows, and each patent is herein incorporated by reference for the supporting teachings:

U.S. Pat. No. 3,613,042, is a variable resistance element with spaced rows of parallel tabs.

U.S. Pat. No. 4,032,881 is a resistance element with improved linearity and method of making the same.

U.S. Pat. No. 4,318,075 is a thick film potentiometer having a wiper track with conductor lines deposited in a parallel fashion.

U.S. Pat. No. 4,500,866 is a nonlinear potentiometer including an arcuate resistor pad connected to a plurality of parallel resistor pads by means of a plurality of conductor lines.

U.S. Pat. No. 4,931,764 is a low wear resistance card for use in a liquid fuel sender card.

U.S. Pat. No. 5,051,719 is a thick-film non-step resistor with accurate resistance characteristics.

U.S. Pat. No. 5,169,465 is a thick-film circuit element on a ceramic substrate.

The foregoing patents reflect the state of the art of which the applicant is aware and are tendered with the view toward discharging applicants' acknowledged duty of candor in disclosing information that may be pertinent in the examination of this application. It is respectfully stipulated, however, that none of these patents teach or render obvious, singly or when considered in combination, applicant's claimed invention.

SUMMARY OF THE INVENTION

It is a feature of the invention to provide a fuel level indicator system. The system uses a resistor card having an arc-shaped resistive path with a first set of spaced apart conductor lines and an arc-shaped resistive ink material overlying the first set of conductor lines. The first conductor lines are formed at an angle with respect to a radial line drawn from the center of the resistive path arc. There is also a first set of glass bars interlaced between the first set of each spaced apart conductor lines. The resistor card also has an arc-shaped continuously solid conductor base and a second set of spaced apart conductor lines extending from the conductor base at an angle with respect to a radial line drawn from the center of the arc-shaped conductor base. There is also second set of glass bars interlaced between the second set of each spaced apart conductor lines.

An additional feature of the invention is to provide a device that includes a wiper assembly having two sets of spaced apart wiper contacts or fingers. One of the fingers in each set engages a first conductor line and a second finger contacts a second adjacent conductor line. The wiper assembly is constructed and arranged to provide rotational movement along both the arc-shaped conductive and resistive path.

A further feature of the invention is to provide a device that has a float and a lever extending from the float connected to the wiper assembly to produce rotational movement of the wiper assembly as the float moves.

The invention resides not in any one of these features per se, but rather in the particular combination of all of them herein disclosed and claimed. Those skilled in the art will appreciate that the conception, upon which this disclosure is based, may readily be utilized as a basis for the designing of other structures, methods and systems for carrying out the several purposes of the present invention. Further, the abstract is neither intended to define the invention of the application, which is measured by the claims, neither is it intended to be limiting as to the scope of the invention in any way.

Figure 1:
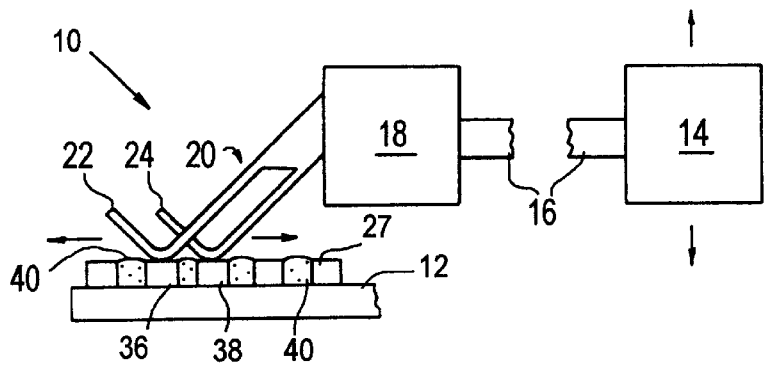
FIG. 1 is a representation of a fuel level detecting system.

It is noted that the drawings of the invention are not to scale. The drawings are merely schematic representations, not intended to portray specific parameters of the invention. The drawings are intended to depict only typical embodiments of the invention, and therefore should not be considered as limiting the scope of the invention. In the drawings, like numbering represents like elements between the drawings.

DETAILED DESCRIPTION OF THE PREFERRED EMBODIMENT

The present invention provides a fuel level detecting system 10 using a unique ceramic card 12 design. Regarding FIG. 1 and FIG. 2, there is fuel float 14 for floating in a fuel tank (not shown). The float 14 is coupled by a coupling 16 to a pivoting wiper linkage 18. Wiper blade assembly 20 is coupled to the pivoting wiper linkage 18 and has two wiper arms 25. Each arm 25 has conductive fingers 21 and 23, and 22 and 24, which are parallel to each other. A ceramic card 12 is used as a base for mounting resistive and conductive traces thereon. Radial lines 32 indicate the pivot point 33 used for determining the parallel arc-shaped design or path of the movable wiper blade assembly 20, arc-shaped resistor trace 30 and arc-shaped solid conductor trace 28. Radial lines 34 indicate the pivot point 35 of radially aligned conductor lines 26 and 27. The resistor trace 30 lies over a portion of each conductor line 27 to form a generally arc shaped resistive path 31. Conductor lines 26 extend from an arc shaped continuously solid conductor base 28 to form a generally arc shaped conductor path 37. There are also insulative segments, in particular, glass bars 40 and 42 that interlaced between each spaced apart conductor line 26 and 27 as illustrated. Fingers 22 and 24 are positioned to contact conductor lines 27 and glass bars 40, and fingers 21 and 23 are positioned to contact conductor lines 26 and glass bars 42 as the wiper blade assembly 20 rotates about point 33.

In operation, as float 14 rises and lowers, coupling 16 moves wiper linkage 18 in a fashion to cause wiper blade assembly 20 to arcuately travel across conductor lines 26 and 27 and glass bars 40 and 42. The moving wiper blade assembly 20 is designed and oriented to have a make-before-break operation, in which the sweeping fingers, ie. 22 and 24 in FIG. 1, make connection with a next conductor line 38 before breaking contact with a currently contacted conductor line 36. Finger 22 would then be disconnected from line 36 while finger 24 is in contact with line 38. Before finger 24 leaves the surface of line 38, finger 22 would come into contact with line 38. Because of the make-before-break design, never will there be an open circuit as a result of non-continuous contact between the fingers and conductor lines as the wiper assembly rotates about point 33.

In assembling, the conductor lines are composed of most any thick film conductor material, typically of an alloy of silver and palladium materials. The conductive lines are applied to the substrate 12 using conventional thick film printing methods. Conductive lines are then fired in a standard thick film furnace. The glass bars are then deposited, typically by screening, between each conductive line. The whole assembly is again fired to form an extremely smooth glass rich surface on the glass bars. The height of the glass bars should closely match the conductive line height to eliminate additional abrasive contact from the metallic contact fingers 21, 22, 23, and 24.

Figure 3:
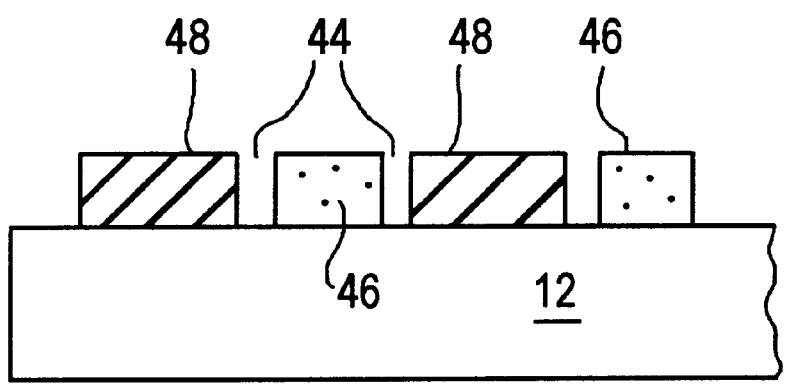
FIG. 3 is a sectional view of the substrate before firing glass bars.

As illustrated in FIG. 3, it is important to leave a space 44 between all sides of the deposited un-fired glass bar 46 and the previously fired conductive lines 48. Spacing prevents harmful covering of the conductive lines during any part of the assembly operation. Covering is especially common during subsequent firing of the glass bars because melting and potential reflow of the glass bars may occur.

Remarks About the Preferred Embodiment

One of ordinary skill in the art of designing and using potentiometers and ceramic cards will realize many advantages from using the preferred embodiment. For example, by having the conductor lines 26 and 27 at a different angle than the angle of rotation and orientation for the fingers 21, 22, 23 and 24 create a make-before-break connection therebetween.

An additional advantage of the preferred embodiment is that the fingers make contact with the conductor lines at an acute angle. A smaller angle of impact will lesson the potential wear on the conductor lines from such impact over thousands of repetitive impacts.

Another advantage of the preferred embodiment is that the acute angle between the fingers and conductor lines prevents open circuit breaks as the wiper blade assembly sweeps across the ceramic card in the make-before-break design.

It is also noted that since the preferred embodiment uses conductor lines instead of a continuous conductive path there is less material used in making the conductor portions, which leads to an overall less expensive part.

Figure 2:
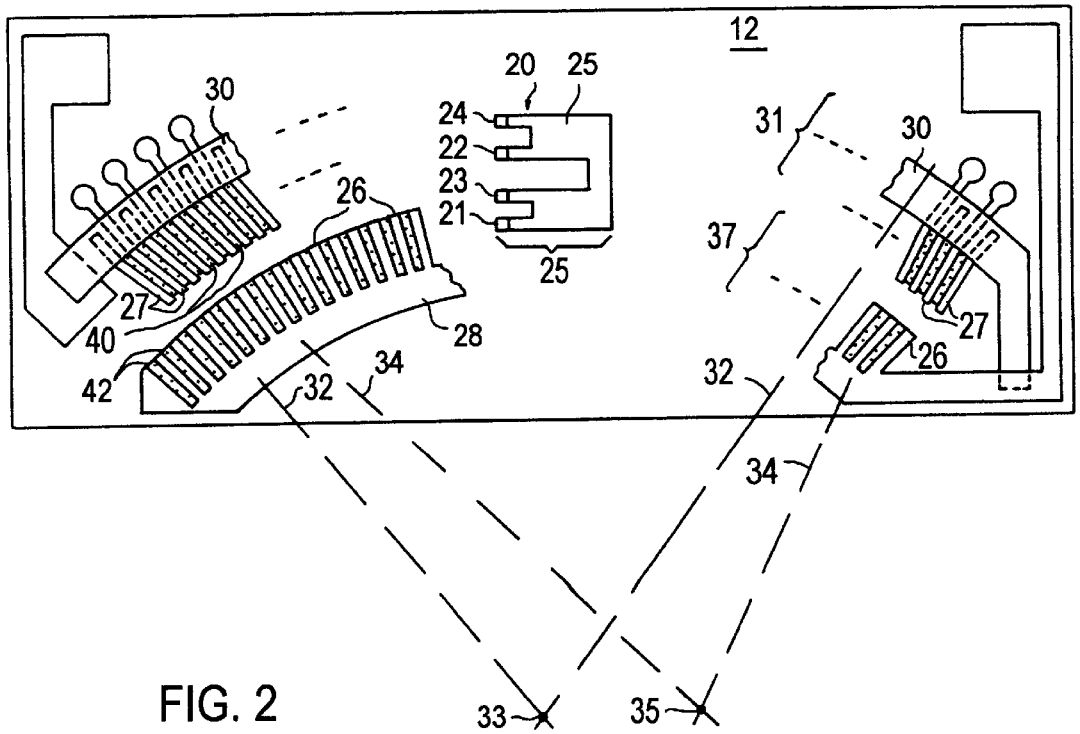
FIG. 2 is a top view of a ceramic resistor card for the fuel level detection system of FIG. 1.

It is noted that FIG. 1 does not illustrate all four contact fingers. It does illustrate the view looking along a radial line 34 as the fingers contact conductor lines 27. It is further noted that resistor trace 30 can be made of resistive ink material.

It is also noted that radial lines 32 and 34 form an angle to each other.

One skilled in the art would understand that the glass bars 40 and 42 would not cover, overlap, sink or bulge relative to the dimensions of conductor lines 26 or 27 to prevent electrical contact to the wiper blade assembly 20. The glass bars 40 and 42 are dimensioned to aid in smooth transition of the wiper blade assembly as it travels between conductor lines by decreasing bumping action or potential wearing of the edges of the conductor lines.

It is noted that since the preferred embodiment is to screen both the conductor lines 26 and 27 and the glass bars 40 and 42. One skilled in the art will realize that there could be air gaps therebetween, unlike, the prior art that has an intimate bonding between the vertical interfacing surfaces as a result of melting. However, it is an option of the preferred embodiment to have heating of the preferred embodiment subsequent to screening the glass bars and conductive lines next to each other. Heating could then create an intimately bonded vertical interfacing surface therebetween and level out the top surfaces contacting the wiper blade assembly.

It is further noted that the preferred embodiment will not have glass from the glass bar material located under the conductive lines 40 and 42 as is common in prior art methods. This allows for more accurate height control between the glass bars and conductive lines.

Variations of the Preferred Embodiment

Although the illustrated embodiment discusses the arrangement of a fuel level sensor one skilled in the art will realize that the preferred embodiment would work with most any type of application besides fuel level sensing. For example, the sensor could be coupled to a computer joy stick or any device needed to sense relatively short positional changes.

Eventhough glass bars 40 and 42 are described as being composed of glass, most any insulative screenable material could work, for example, glass frit mixtures, or ceramic pastes.

Although coupling 16 is ambiguously illustrated, it is contemplated that coupling could be a mechanical lever, a cable, or even an electronically controlled position sensor actuator assembly.

Although wiper linkage 18 is ambiguously illustrated, it is contemplated that the linkage could be a rotatable housing with a pivot point fixed relative to point 33.

One skilled in the art will realize that wiper blade assembly 20 could be designed with many variations. For example, three or more fingers could be used on each wiper arm 25, or button-shaped indents on the bottom side of the fingers could be used.

A skilled artisan will understand that there are many ways to complete the linkage between the float mechanism 14 and the pivoting wiper blade linkage. For example, a cable connection that twists as the float moves thus moving the wiper blade assembly, or just connection of the float to an arm that is pivotally mounted to a housing of the substrate 12 that causes the wiper blade assembly 20 to rotate as the float rises and lowers.

While the invention has been taught with specific reference to these embodiments, someone skilled in the art will recognize that changes can be made in form and detail without departing from the spirit and the scope of the invention. The described embodiments are to be considered in all respects only as illustrative and not restrictive. The scope of the invention is, therefore, indicated by the appended claims rather than by the description. All changes that come within the meaning and range of equivalency of the claims are to be embraced within their scope.

What is claimed and desired to be secured by patent is:

1. A fuel level indicator system, comprising:
   a) a substrate having an arc-shaped resistive path including a first set of spaced apart conductor lines and an arc-shaped resistive ink material overlying said first set of conductor lines and extending above the substrate;
   b) an arc-shaped continuously solid conductor base and a second set of spaced apart conductor lines extending from said base and extending above the substrate;
   c) a wiper having a pair of spaced apart arms, each arm having a plurality of parallel fingers extending from one end such that one of said fingers on a first arm engages a conductor line on the resistive path and a second finger on said first arm engages an adjacent conductor line along said resistive path; and a first finger on said second arm engages a conductive line on said conductive path and a second finger engaging an adjacent conductor line on said conductive path; and
   d) a first and second set of insulative bars located between and parallel to the first and second sets of spaced apart conductor lines, respectively, the insulative bars extending above the substrate and relatively co-planar with the first and second sets of spaced apart conductor lines such that the wiper is continuously in contact with either the conductor lines or the insulative bars, the insulative bars preventing the wiper from contacting the substrate and providing reduced wear on the wiper and longer life.

2. The fuel level indicator system as set forth in claim 1, wherein the first and second set of insulative bars are a screenably deposited and fired glass.

3. The fuel level indicator system as set forth in claim 2, wherein a space is located between the insulative bars and the conductor lines.

* * * * *